(12) United States Patent
Chanduszko (10) Patent No.: US 7,704,268 B2
(45) Date of Patent: Apr. 27, 2010

(54) CLOSURE DEVICE WITH HINGES

(75) Inventor: Andrzej J. Chanduszko, Chandler, AZ (US)

(73) Assignee: NMT Medical, Inc., Boston, MA (US)

( * ) Notice: Subject to any disclaimer, the term of this patent is extended or adjusted under 35 U.S.C. 154(b) by 526 days.

(21) Appl. No.: 11/111,685

(22) Filed: Apr. 21, 2005

(65) Prior Publication Data

US 2005/0288786 A1 Dec. 29, 2005

Related U.S. Application Data

(60) Provisional application No. 60/569,203, filed on May 7, 2004.

(51) Int. Cl.
*A61B 17/08* (2006.01)

(52) U.S. Cl. ..................................................... 606/213

(58) Field of Classification Search ................ 606/151, 606/153, 213, 215, 216, 200, 157; 604/107–109; 128/830, 831; 623/1.35, 1.37
See application file for complete search history.

(56) References Cited

U.S. PATENT DOCUMENTS

| | | | |
|---|---|---|---|
| 3,874,388 A | 4/1975 | King at al. |
| 3,875,648 A | 4/1975 | Bone |
| 4,006,747 A | 2/1977 | Kronenthal et al. |
| 4,007,743 A | 2/1977 | Blake |
| 4,425,908 A | 1/1984 | Simon |
| 4,696,300 A | 9/1987 | Anderson |
| 4,710,192 A | 12/1987 | Liotta et al. |
| 4,836,204 A | 6/1989 | Landymore et al. |
| 4,902,508 A | 2/1990 | Badylak et al. |
| 4,915,107 A | 4/1990 | Rebuffat et al. |
| 4,917,089 A | 4/1990 | Sideris |
| 4,956,178 A | 9/1990 | Badylak et al. |
| 5,021,059 A | 6/1991 | Kensey et al. |
| 5,037,433 A | 8/1991 | Wilk et al. |
| 5,041,129 A | 8/1991 | Hayhurst et al. |
| 5,108,420 A | 4/1992 | Marks |

(Continued)

FOREIGN PATENT DOCUMENTS

DE 94 13 645 U1 10/1994

(Continued)

OTHER PUBLICATIONS

International Search Report, International Application No. PCT/US03/17390, mailed Oct. 6, 2003 (4 pgs).

(Continued)

*Primary Examiner*—(Jackie) Tan-Uyen T. Ho
*Assistant Examiner*—Dianne Dornbusch
(74) *Attorney, Agent, or Firm*—Helen S. Liu (57) ABSTRACT

A device for closing a defect, such as a patent foramen ovale (PFO) or an atrial septal defect (ASD), has first and second sides on either side of the defect, a center joint that passes through the defect, and end pieces at the outer ends of the sides. One or both sides of the device have a plurality of petals. At least one petal on each side extends away from the center joint, and at least one petal on each side extends away from an end piece. Adjacent petals are coupled together with hinges.

24 Claims, 13 Drawing Sheets

U.S. PATENT DOCUMENTS

| | | | |
|---|---|---|---|
| 5,171,259 A | 12/1992 | Inoue | |
| 5,192,301 A | 3/1993 | Kamiya et al. | |
| 5,222,974 A | 6/1993 | Kensey et al. | |
| 5,236,440 A | 8/1993 | Hlavacek | |
| 5,257,637 A | 11/1993 | El Gazayerli | |
| 5,275,826 A | 1/1994 | Badylak et al. | |
| 5,282,827 A | 2/1994 | Kensey et al. | |
| 5,284,488 A | 2/1994 | Sideris | |
| 5,304,184 A | 4/1994 | Hathaway et al. | |
| 5,312,341 A | 5/1994 | Turi | |
| 5,312,435 A | 5/1994 | Nash et al. | |
| 5,334,217 A | 8/1994 | Das | |
| 5,354,308 A | 10/1994 | Simon et al. | |
| 5,411,481 A | 5/1995 | Allen et al. | |
| 5,413,584 A | 5/1995 | Schulze | |
| 5,417,699 A | 5/1995 | Klein et al. | |
| 5,425,744 A | 6/1995 | Fagan et al. | |
| 5,433,727 A | 7/1995 | Sideris | |
| 5,451,235 A | 9/1995 | Lock et al. | |
| 5,478,353 A | 12/1995 | Yoon | |
| 5,480,424 A | 1/1996 | Cox | |
| 5,486,193 A | 1/1996 | Bourne et al. | |
| 5,507,811 A | 4/1996 | Koike et al. | |
| 5,540,712 A | 7/1996 | Kleshinski et al. | |
| 5,577,299 A | 11/1996 | Thompson et al. | |
| 5,601,571 A | 2/1997 | Moss | |
| 5,618,311 A | 4/1997 | Gryskiewicz | |
| 5,620,461 A | 4/1997 | Muijs Van De Moer et al. | |
| 5,626,599 A | 5/1997 | Bourne et al. | |
| 5,634,936 A | 6/1997 | Linden et al. | |
| 5,649,950 A | 7/1997 | Bourne et al. | |
| 5,683,411 A | 11/1997 | Kavteladze et al. | |
| 5,693,085 A | 12/1997 | Buirge et al. | |
| 5,702,421 A | 12/1997 | Schneidt | |
| 5,709,707 A | 1/1998 | Lock et al. | |
| 5,720,754 A | 2/1998 | Middleman et al. | |
| 5,725,552 A | 3/1998 | Kotula et al. | |
| 5,733,294 A | 3/1998 | Forber et al. | |
| 5,733,337 A | 3/1998 | Carr, Jr. et al. | |
| 5,741,297 A | 4/1998 | Simon | |
| 5,776,162 A | 7/1998 | Kleshinski | |
| 5,797,960 A | 8/1998 | Stevens et al. | |
| 5,800,516 A | 9/1998 | Fine et al. | |
| 5,810,884 A | 9/1998 | Kim | |
| 5,823,956 A | 10/1998 | Roth et al. | |
| 5,829,447 A | 11/1998 | Stevens et al. | |
| 5,853,422 A | 12/1998 | Huebsch et al. | |
| 5,855,614 A | 1/1999 | Stevens et al. | |
| 5,861,003 A | 1/1999 | Latson et al. | |
| 5,865,791 A | 2/1999 | Whayne et al. | |
| 5,879,366 A | 3/1999 | Shaw et al. | |
| 5,893,856 A | 4/1999 | Jacob et al. | |
| 5,902,319 A | 5/1999 | Daley | |
| 5,904,703 A | 5/1999 | Gilson | |
| 5,919,200 A | 7/1999 | Stambaugh et al. | |
| 5,924,424 A | 7/1999 | Stevens et al. | |
| 5,928,250 A | 7/1999 | Koike et al. | |
| 5,944,738 A | 8/1999 | Amplatz et al. | |
| 5,955,110 A | 9/1999 | Patel et al. | |
| 5,976,174 A | 11/1999 | Ruiz | |
| 5,989,268 A | 11/1999 | Pugsley, Jr. et al. | |
| 5,993,475 A | 11/1999 | Lin et al. | |
| 5,993,844 A | 11/1999 | Abraham et al. | |
| 5,997,575 A | 12/1999 | Whitson et al. | |
| 6,010,517 A | 1/2000 | Baccaro | |
| 6,024,756 A | 2/2000 | Huebsch et al. | |
| 6,030,007 A | 2/2000 | Bassily et al. | |
| 6,056,760 A | 5/2000 | Koike et al. | |
| 6,077,291 A | 6/2000 | Das | |
| 6,079,414 A | 6/2000 | Roth | |
| 6,080,182 A | 6/2000 | Shaw et al. | |
| 6,096,347 A | 8/2000 | Gedees et al. | |
| 6,106,913 A | 8/2000 | Scardino et al. | |
| 6,113,609 A | 9/2000 | Adams | |
| 6,117,159 A * | 9/2000 | Huebsch et al. | 606/213 |
| 6,126,686 A | 10/2000 | Badylak et al. | |
| 6,132,438 A | 10/2000 | Fleischman et al. | |
| 6,143,037 A | 11/2000 | Goldstein et al. | |
| 6,152,144 A | 11/2000 | Lesh et al. | |
| 6,165,183 A | 12/2000 | Kuehn et al. | |
| 6,165,204 A | 12/2000 | Levinson et al. | |
| 6,171,329 B1 | 1/2001 | Shaw et al. | |
| 6,174,322 B1 | 1/2001 | Schneidt | |
| 6,187,039 B1 | 2/2001 | Hiles et al. | |
| 6,206,895 B1 | 3/2001 | Levinson | |
| 6,206,907 B1 | 3/2001 | Marino et al. | |
| 6,214,029 B1 * | 4/2001 | Thill et al. | 606/213 |
| 6,217,590 B1 | 4/2001 | Levinson | |
| 6,221,092 B1 | 4/2001 | Koike et al. | |
| 6,228,097 B1 | 5/2001 | Levinson et al. | |
| 6,231,561 B1 | 5/2001 | Frazier et al. | |
| 6,245,080 B1 | 6/2001 | Levinson | |
| 6,265,333 B1 | 7/2001 | Dzenis et al. | |
| 6,270,515 B1 | 8/2001 | Linden et al. | |
| 6,277,138 B1 | 8/2001 | Levinson et al. | |
| 6,277,139 B1 | 8/2001 | Levinson et al. | |
| 6,287,317 B1 | 9/2001 | Makower et al. | |
| 6,290,674 B1 | 9/2001 | Roue et al. | |
| 6,306,150 B1 | 10/2001 | Levinson | |
| 6,306,424 B1 | 10/2001 | Vyakarnam et al. | |
| 6,312,446 B1 | 11/2001 | Huebsch et al. | |
| 6,319,263 B1 | 11/2001 | Levinson | |
| 6,322,548 B1 | 11/2001 | Payne et al. | |
| 6,328,727 B1 | 12/2001 | Frazier et al. | |
| 6,334,872 B1 | 1/2002 | Termin et al. | |
| 6,342,064 B1 | 1/2002 | Koike et al. | |
| 6,344,049 B1 | 2/2002 | Levinson et al. | |
| 6,346,074 B1 | 2/2002 | Roth | |
| 6,348,041 B1 | 2/2002 | Klint | |
| 6,352,552 B1 | 3/2002 | Levinson et al. | |
| 6,355,052 B1 | 3/2002 | Neuss et al. | |
| 6,364,853 B1 | 4/2002 | French et al. | |
| 6,375,625 B1 | 4/2002 | French et al. | |
| 6,375,671 B1 | 4/2002 | Kobayashi et al. | |
| 6,379,342 B1 | 4/2002 | Levinson | |
| 6,379,368 B1 | 4/2002 | Corcoran et al. | |
| 6,387,104 B1 | 5/2002 | Pugsley, Jr. et al. | |
| 6,398,796 B2 | 6/2002 | Levinson | |
| 6,402,772 B1 | 6/2002 | Amplatz et al. | |
| 6,419,669 B1 | 7/2002 | Frazier et al. | |
| 6,436,088 B2 | 8/2002 | Frazier et al. | |
| 6,440,152 B1 | 8/2002 | Gainor et al. | |
| 6,460,749 B1 | 10/2002 | Levinson et al. | |
| 6,482,224 B1 | 11/2002 | Michter et al. | |
| 6,488,706 B1 | 12/2002 | Solymar | |
| 6,494,888 B1 | 12/2002 | Laufer et al. | |
| 6,551,303 B1 | 4/2003 | Van Tassel et al. | |
| 6,551,344 B2 | 4/2003 | Thill | |
| 6,596,013 B2 | 7/2003 | Yang et al. | |
| 6,623,508 B2 | 9/2003 | Shaw et al. | |
| 6,623,518 B2 | 9/2003 | Thompson et al. | |
| 6,666,861 B1 | 12/2003 | Grabek | |
| 6,712,804 B2 | 3/2004 | Roue et al. | |
| 6,712,836 B1 | 3/2004 | Berg et al. | |
| 6,726,696 B1 | 4/2004 | Houser et al. | |
| 7,165,552 B2 * | 1/2007 | Deem et al. | 128/898 |
| 2001/0014800 A1 | 8/2001 | Frazier et al. | |
| 2001/0034537 A1 | 10/2001 | Shaw et al. | |
| 2001/0037129 A1 | 11/2001 | Thill | |
| 2001/0039435 A1 | 11/2001 | Roue et al. | |
| 2001/0041914 A1 | 11/2001 | Frazier et al. | |
| 2001/0041915 A1 | 11/2001 | Roue et al. | |
| 2001/0044639 A1 | 11/2001 | Levinson | |
| 2001/0049492 A1 | 12/2001 | Frazier et al. | |

| | | |
|---|---|---|
| 2002/0010481 A1 | 1/2002 | Jayaraman |
| 2002/0019648 A1 | 2/2002 | Akerfeldt et al. |
| 2002/0026208 A1 | 2/2002 | Roe et al. |
| 2002/0029048 A1 | 3/2002 | Miller |
| 2002/0032462 A1 | 3/2002 | Houser et al. |
| 2002/0035374 A1 | 3/2002 | Borillo et al. |
| 2002/0043307 A1 | 4/2002 | Ishida et al. |
| 2002/0052572 A1 | 5/2002 | Franco et al. |
| 2002/0077555 A1 | 6/2002 | Schwartz |
| 2002/0096183 A1 | 7/2002 | Stevens et al. |
| 2002/0099389 A1 | 7/2002 | Michler et al. |
| 2002/0107531 A1 | 8/2002 | Schreck et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0169377 A1 | 11/2002 | Khairkhahan et al. |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 | 12/2002 | Gainor |
| 2003/0028213 A1 | 2/2003 | Thill et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0059640 A1 | 3/2003 | Marton et al. |
| 2003/0065379 A1 | 4/2003 | Babbas et al. |
| 2003/0100920 A1 | 5/2003 | Akin et al. |
| 2003/0139819 A1 | 7/2003 | Beer et al. |
| 2003/0171774 A1 | 9/2003 | Freudenthal et al. |
| 2003/0191495 A1 | 10/2003 | Ryan et al. |
| 2003/0195530 A1 | 10/2003 | Thill |
| 2003/0204203 A1 | 10/2003 | Khairkhahan et al. |
| 2004/0044361 A1 | 3/2004 | Frazier et al. |
| 2004/0073242 A1 | 4/2004 | Chanduszko |
| 2004/0210301 A1 | 10/2004 | Obermiller |
| 2005/0043759 A1 | 2/2005 | Chanduszko |

FOREIGN PATENT DOCUMENTS

| | | |
|---|---|---|
| EP | 0 362 113 | 4/1990 |
| EP | 0 474 887 | 3/1992 |
| EP | 1 013 227 A2 | 6/2000 |
| EP | 1 046 375 | 10/2000 |
| EP | 1 222 897 | 7/2002 |
| WO | WO-96/25179 | 8/1996 |
| WO | WO-96/31157 | 10/1996 |
| WO | WO-98/07375 A1 | 2/1998 |
| WO | WO-99/05977 A1 | 2/1999 |
| WO | WO-99/18862 A1 | 4/1999 |
| WO | WO-99/18864 A1 | 4/1999 |
| WO | WO-99/18870 A1 | 4/1999 |
| WO | WO-99/18871 A1 | 4/1999 |
| WO | WO-99/30640 | 6/1999 |
| WO | WO-00/27292 | 5/2000 |
| WO | WO-00/44428 | 8/2000 |
| WO | WO-01/21247 A1 | 3/2001 |
| WO | WO-01/30268 A1 | 5/2001 |
| WO | WO-01/49185 | 7/2001 |
| WO | WO-01/78596 A1 | 10/2001 |
| WO | WO-02/17809 A1 | 3/2002 |
| WO | WO-02/24106 | 3/2002 |
| WO | WO-03/077733 | 9/2003 |
| WO | WO-03/103476 A | 12/2003 |

OTHER PUBLICATIONS

Kimura, A., et al., "Effects of Neutron Irradiation on the Transformation Behavior in Ti-Ni Alloys," Abstract, Proceedings of the Int'l Conf. on Mariensitic Transformations, 1992, pp. 935-940.

Meier, MD, Bernhard et al., "Contemporary Management of Patent Foramen Ovale," American Heart Association, Inc., Circulation, 2003, vol. 107, pp. 5-9.

Nat'l Aeronautics and Space Administration, "55-Nitinol—The Alloy with a Memory: Its Physical Metalurgy, Properties and Applications," NASA Report, pp. 24-25.

Ramanathan, G., et al., "Experimental and Computational Methods for Shape Memory Alloys," 15th ASCE Engineering Mechanics Conference, Jun. 2-5, 2002.

Ruiz, et al, "The Puncture Technique: A New Method for Transcatheter Closure of Patent Foramen Ovale," Catheterization and Cardiovascular Interventions, 2001, vol. 53, pp. 369-372.

Shabalovskaya, S., "Surface, Corrosion and Biocompatibliity Aspects of Nitinol as an Implant Material," Bio-Medical Materials and Engineering, 2002, vol. 12, pp. 69-109.

SMST-2000, "Proceedings of the International Conference on Shape Memory and Superelastic Technologies," Apr. 30 to May 4, 2000, Asilomar Conference Center.

Stockel, "Nitinol Medical Devices and Implants," SMST-2000 Conference Proceedings, 2001, pp. 531-541.

Uchil, J., "Shape Memory Alloys—Characterization Techniques," Pramana—Journal of Physics, 2002, vol. 58(5)(6), pp. 1131-1139.

* cited by examiner

CLOSURE DEVICE WITH HINGES

CROSS-REFERENCE TO RELATED APPLICATION

This application claims priority to provisional application Ser. No. 60/569,203, filed May 7, 2004, which is incorporated herein by reference.

BACKGROUND

This invention relates to an occluder for closing a septal defect, such as a patent foramen ovale (PFO).

Figure 1:
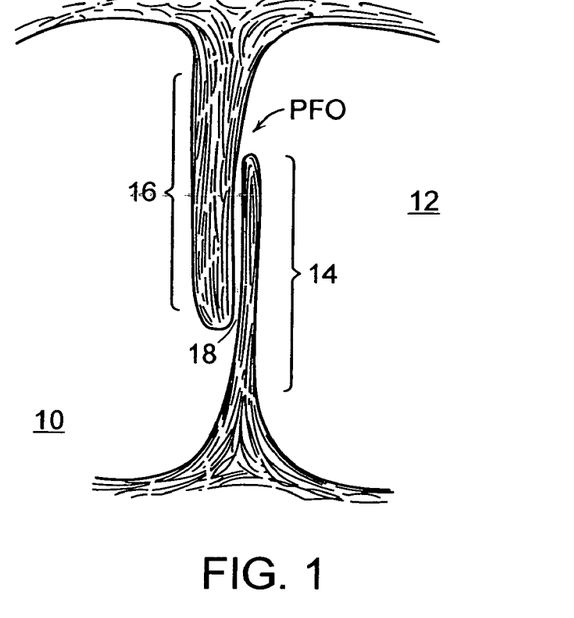
FIG. 1 is a part side, part cross-sectional view showing a patent foramen ovale (PFO).

A PFO, illustrated in FIG. 1, is a persistent, one-way, usually flap-like opening in the wall between the right atrium 10 and left atrium 12 of the heart. Because left atrial pressure is normally higher than right atrial pressure, the flap formed by septum primum 14 and septum secundum 16 usually stays closed. Under certain conditions, however, right atrial pressure can exceed left atrial pressure, which creates the possibility that blood could pass from the right atrium to the left atrium through a PFO tunnel 18 and allow blood clots to enter the systemic circulation. It is desirable to avoid this situation.

SUMMARY

The present invention relates to a device for closing a defect, such as a PFO or an atrial septal defect (ASD). In preferred embodiments, the device has first and second sides on either side of the defect, a center joint that passes through the defect, and end pieces at the outer ends of the sides. One or both sides of the device have a plurality of petals. At least one petal on each side extends away from the center joint, and at least one petal on each side extends away from an end piece. Adjacent petals are coupled together with hinges.

The end pieces, center joint, and petals can be made from multiple pieces integrally connected, or from a monolithic material, such as from a single tube. If a single tube is used as a starting material, it is cut with slits in desired locations to produce the device when the ends are brought toward each other. The device can be roughened or textured, and can have a spongy collar around the center joint. A catching mechanism can be provided to hold the device in place when deployed.

Embodiments of this device can provide one or more of the following benefits: small diameter delivery sheath, no permanent foreign material, ease of manufacturing, and overall simplicity. Other features and advantages will become apparent from the following detailed description, drawings, and claims.

DETAILED DESCRIPTION

Figure 5:
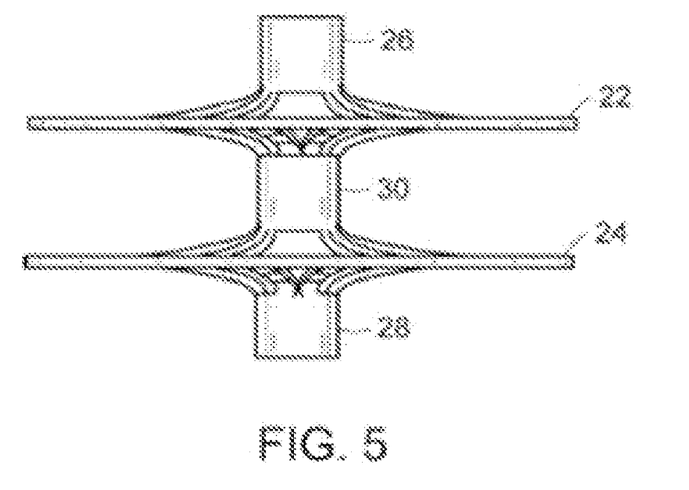
Figure 6:
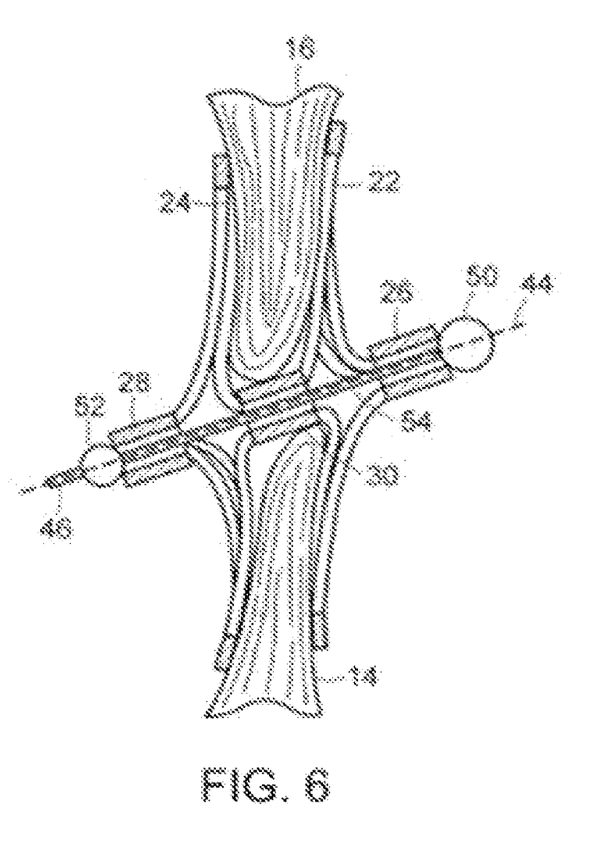
FIG. 6 is a partial side, partial cross sectional view of the device of FIG. 2 shown as deployed in the PFO.
Figures 7, 8:
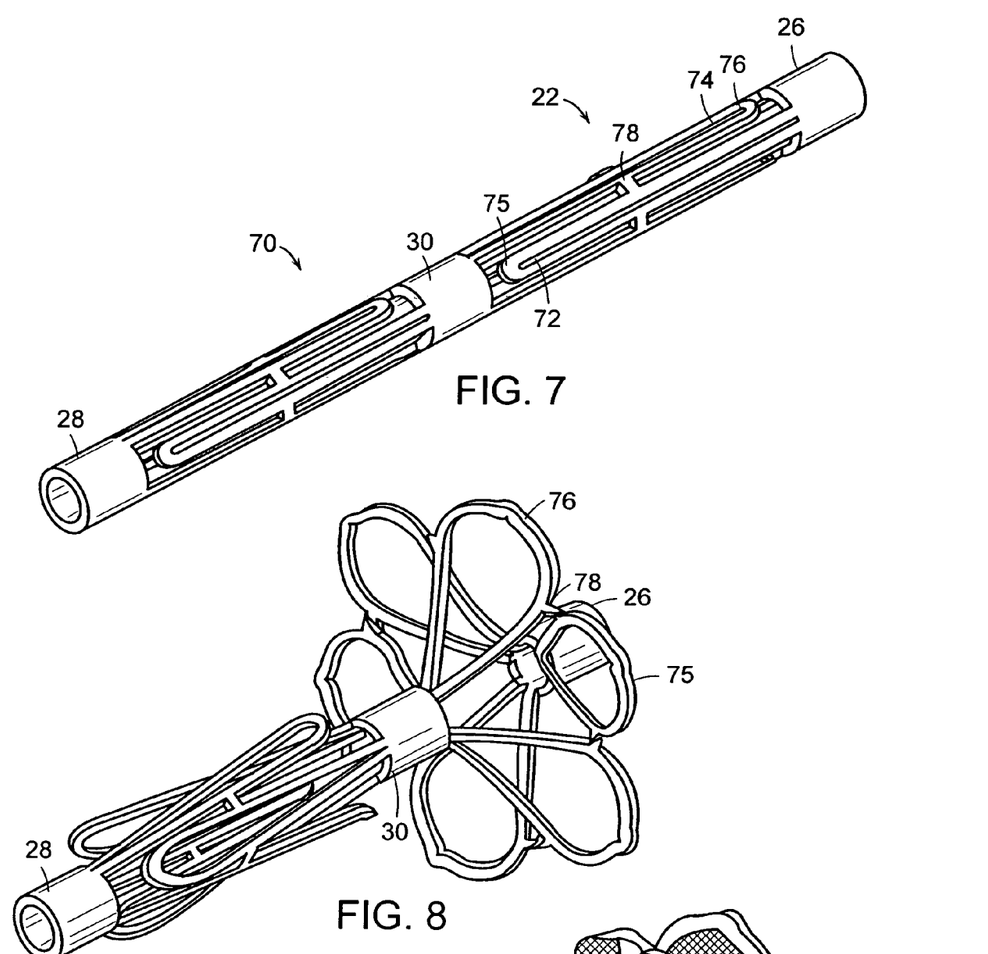
FIG. 7 is a perspective view of a tube that is cut to produce the device of the type shown in FIG. 2.
FIG. 8 is a perspective view of the device of FIG. 7 shown in a partially open form.

Embodiments of an occluding device are shown in FIGS. 2-9, with the delivery process illustrated in FIGS. 10-13, and recovery processes in FIGS. 15-19 and FIGS. 20-22. The device can be formed from a polymer tube, as shown in FIG. 7, by making cuts in the tube. This approach is similar in general to that described in application Ser. No. 60/486,992, filed Jul. 14, 2003, and application Ser. No. 60/557,486, filed Mar. 3, 2004, each of which is incorporated herein by reference. Other catching or locking methods in addition to those described below, some or all of which may be adaptable to devices of the type described herein, are described in application Ser. No. 60/569,422, filed on May 7, 2004, which is incorporated herein by reference.

Figure 2:
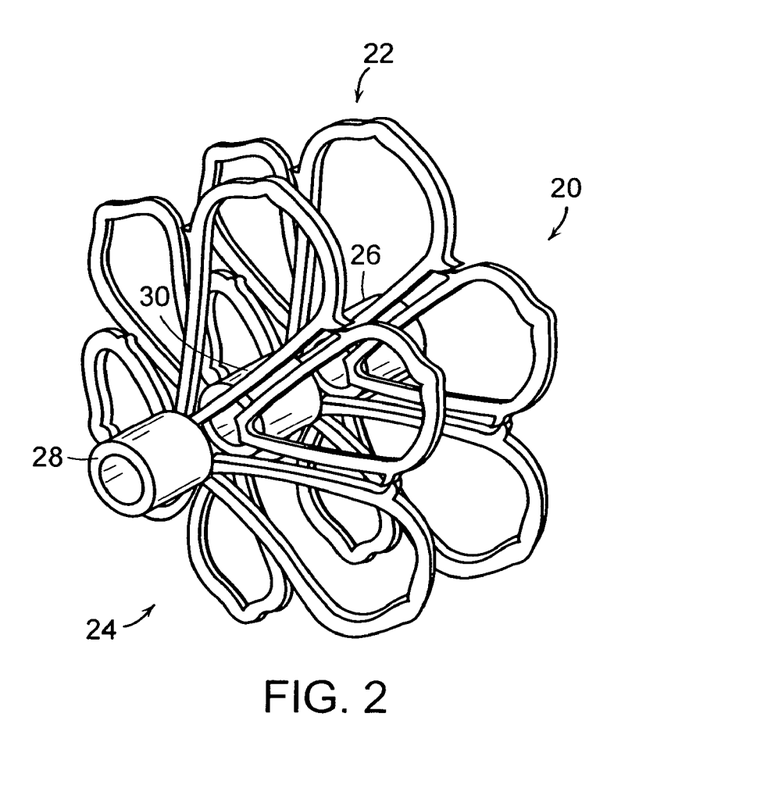
FIG. 2 is a perspective view of a closure device according to a first embodiment of the present invention.
Figure 4:
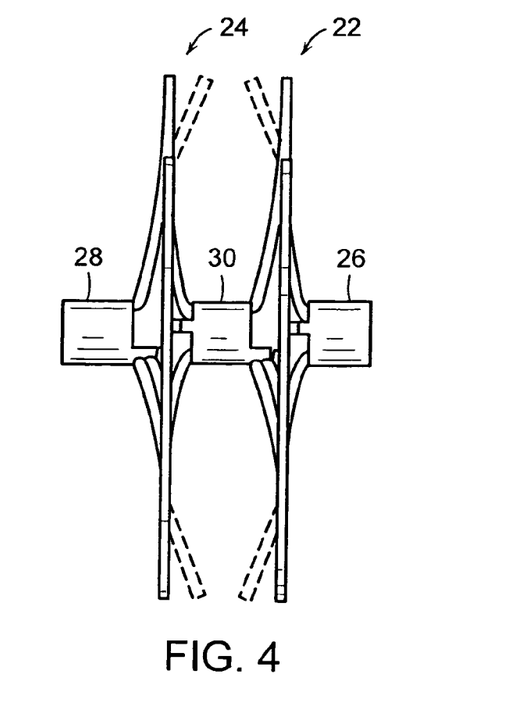

Referring particularly to FIGS. 2, 4, and 5, a device 20 has a distal (left atrial) side 22 and a proximal (right atrial) side 24. Sides 22 and 24 are each connected to and separated by a center joint 30. At the outer ends of sides 22 and 24 are respective end pieces 26 and 28. The end piece and center joint each have a preferably tubular hollow configuration.

Figure 3:
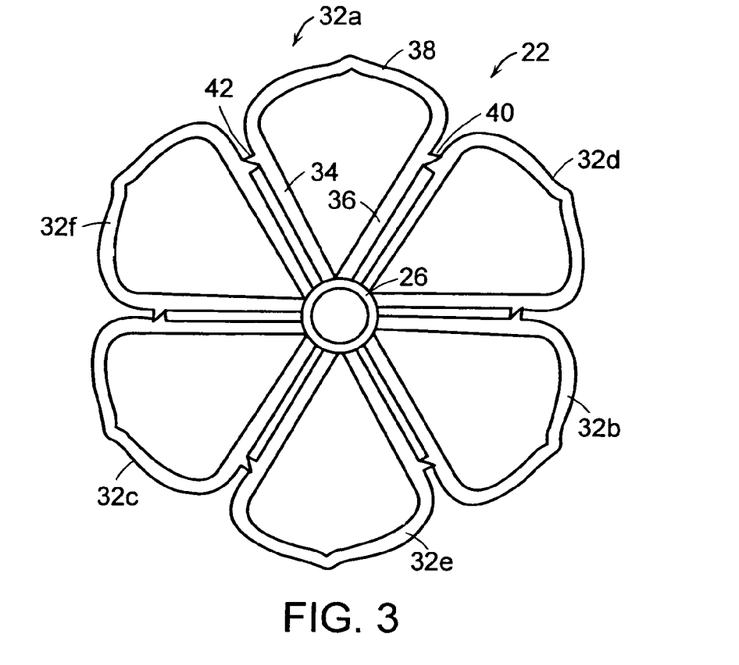
FIGS. 3-5 are a plan view and side views of the device of FIG. 2.

Referring also to FIG. 3, an end view shows distal side 22 with end piece 26 in the center. The view from the right atrial side at side 24 would be substantially the same as this view in this embodiment. Side 22 has a plurality of petals, preferably six petals 32a-32f as shown, although more or fewer petals could be used. Referring to petal 32a in FIG. 3 as an example, each petal includes two segments 34 and 36, preferably substantially straight, that come together or close to each other at a vertex, and a rounded portion 38 at the outer perimeter of the petal. Each petal is connected to an adjacent petal through a short hinge, such as hinges 40 and 42 shown in FIG. 3. The term vertex is used broadly here to include the situations where the sides that extend away from the center joint (or end piece) to form a petal meet at the center joint, or where the sides that form the petal meet at a point slightly spaced outwardly from the center joint, or where the sides have not fully converged to a point at the center joint and therefore have not yet come together.

Referring particularly to FIGS. 2 and 8, the petals preferably have an alternating arrangement such that every other petal has a vertex at an end piece, with the petals between them having a vertex at the center joint. FIG. 8 provides a good view of this structure in which alternating petals are connected together with hinges and yet have their vertices coupled at alternating ends. While shown as identical in size, the petals that extend away from the center joint may be made shorter than those that extend away from one of the two end pieces.

The petals are preferably substantially the same size and shape, and are evenly distributed around the circumference of the device, although petal sizes can be varied and, as indicated above, different numbers of petals can be used. The configuration of petals can be different on different sides of the defect.

As indicated especially in FIGS. 4-6, sides 22 and 24 can have a roughly planar configuration in a manner that is roughly parallel to the opening. While the sides are shown as being exactly parallel in FIGS. 4 and 5, the device would typically be formed so that the sides are bowed such that the ends of sides 22 and 24 are closer to each other than the sides are at the middle, as shown in dashed lines in FIG. 4. As shown in FIG. 6, the sides preferably have the ability to bend and conform to the geometry of the opening. The sides of the occluder have a diameter that can be in the range, for example, of 15-45 mm, while other sizes could be used. While the sides are shown with substantially identical diameter in FIGS. 4 and 5, they need not have the same diameter and could be shorter on one side. It is preferable for a large portion of the perimeter of the petals to be in contact with each septum to distribute forces and provide less trauma than might otherwise be provided if all the force for each petal were at one point. This means that each petal preferably forms a plane that is generally parallel with each septum, rather than perpendicular.

Referring particularly to FIG. 6, in a deployed form, sides 22 and 24 each have upper portions against septum secundum 16, and lower portions against septum primum 14. A catching mechanism is used to help hold the device in place. As shown here, the catching mechanism includes balls 50 and 52 connected with a hollow conduit 54. Balls 50 and 52 help to hold the device in a compressed position by helping to hold together end pieces 26 and 28.

Ball 50, ball 52, and wire 54 preferably all have an aligned central bore through the middle, represented as line 44, to allow the catching mechanism to be delivered over a small wire (not shown). A hollow delivery wire 46 is releasably connected and detached from ball 52 through one of a number of techniques, such as a threaded connection.

Referring to FIG. 7, the device is preferably formed from a hollow tube 70 with cuts to the tube to define the structures of the device. End pieces 26 and 28 and center joint 30 in this embodiment are characterized by a lack of cuts, although there could be some for desired bending or flexing. Each side is shown here as substantially identical, although each side could be cut differently, such that only one side has the structure shown in FIG. 3. In addition, while the center joint 30 is shown about an equal distance between the ends, it can be provided more toward one end if it is desirable for the device to have different diameters on either side of the device. In the tube, cuts defining a slot 72, 74 with one end at the end piece (in the case of slot 72) or the center joint (in the case of slot 74) and another end of the slots 75, 76 being rounded to form a petal when the end pieces of the device are brought toward each other. Short circumferential segments, such as segment 78, between these slots 72 and 74 define the hinges when the device is deployed.

FIG. 8 shows the device taking shape when end piece 26 is brought to center joint 30. Rounded ends 76 and 75 are at the outer ends of petals that extend from the center joint and end piece, respectively. End piece 28 is shown as it is beginning to be brought toward center joint 30. After both sides take their shape, the device can be further thermally and mechanically processed to help it maintain its shape in the manufactured configuration and in the deployed configuration.

Figure 9:
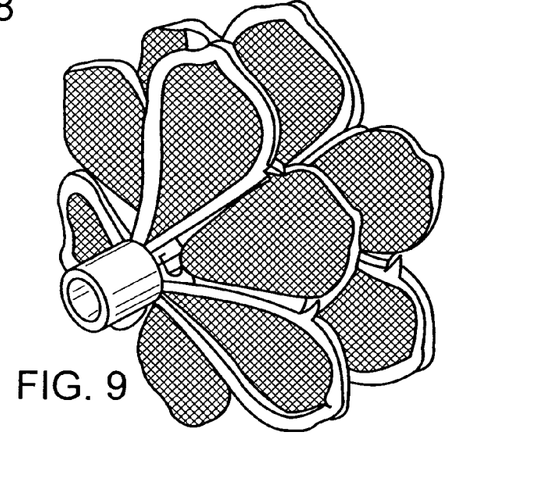
FIG. 9 is a perspective view of the device of FIGS. 2-8 with a tissue scaffold.

Referring to FIG. 9, a tissue scaffold can be provided over area defined by some or all of the petals, and around the petals themselves if desired. The tissue scaffold promotes encapsulation and endothelialization, thereby further encouraging anatomical closure of septum primum and septum secundum. A tissue scaffold can be formed of any flexible, biocompatible material capable of promoting tissue growth, including but not limited to polyester fabrics, Teflon-based materials, such as ePTFE, polyurethanes, metallic materials, polyvinyl alcohol (PVA), extracellular matrix (ECM) or other bioengineered materials, synthetic bioabsorbable polymeric scaffolds, other natural materials (e.g. collagen), or combinations of these materials. Also tissue scaffold may be formed of a thin metallic film or foil. The scaffold can be attached to one or both sides of the device. A tissue scaffold or the body of the device frame can have drugs or biological agents to improve the defect healing process and/or to prevent clotting.

With a tissue scaffold that blocks blood flow, this device can be used for atrial septal defects. One difference between an ASD occluder versus a PFO occluder is that in an ASD occluder, the device may have to help block blood flow because the defect is an opening, while the PFO occluder can function as an occluder by holding together existing flaps. The tissue scaffold could be used for an occluder made for either type of defect.

Figure 10:
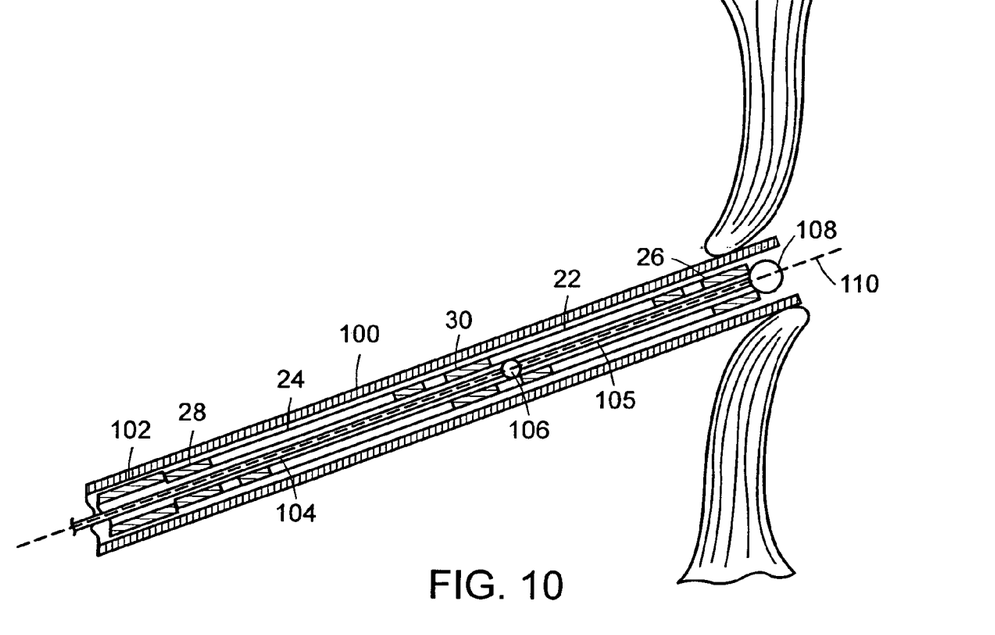
FIGS. 10-13 are part side, part cross-sectional views showing the deployment of devices with a catching mechanism according to embodiments of the present invention.

FIGS. 10-13 show an example of the delivery of the device with a catching mechanism. As shown in FIG. 10, the device with end pieces 26 and 28, center joint 30, and sides 22 and 24, are loaded into a delivery sheath 100. An inner catheter 102 is used to hold the device in place to prevent it from being pulled toward the proximal end when that movement is not desired. A wire 104 extends coaxially through sheath 100, and is releasably connected to the catching mechanism that includes ball 106, which is rigidly connected through a connecting wire 105 to ball 108. Examples of releasable connections (not shown in FIG. 10) are described below in conjunction with FIGS. 14A and 14B. Wire 104, wire 105, ball 106, and ball 108 all preferably have aligned hollow openings to allow a guide wire 110 to pass through. Guide wire 110 is used for positioning and to assist with the delivery. Ball 108 can be held in place by inward force against end piece 26 without being bonded or clamped or otherwise connected to end piece 26, or it can be so rigidly connected and permanently attached to end piece 26.

Figure 11:
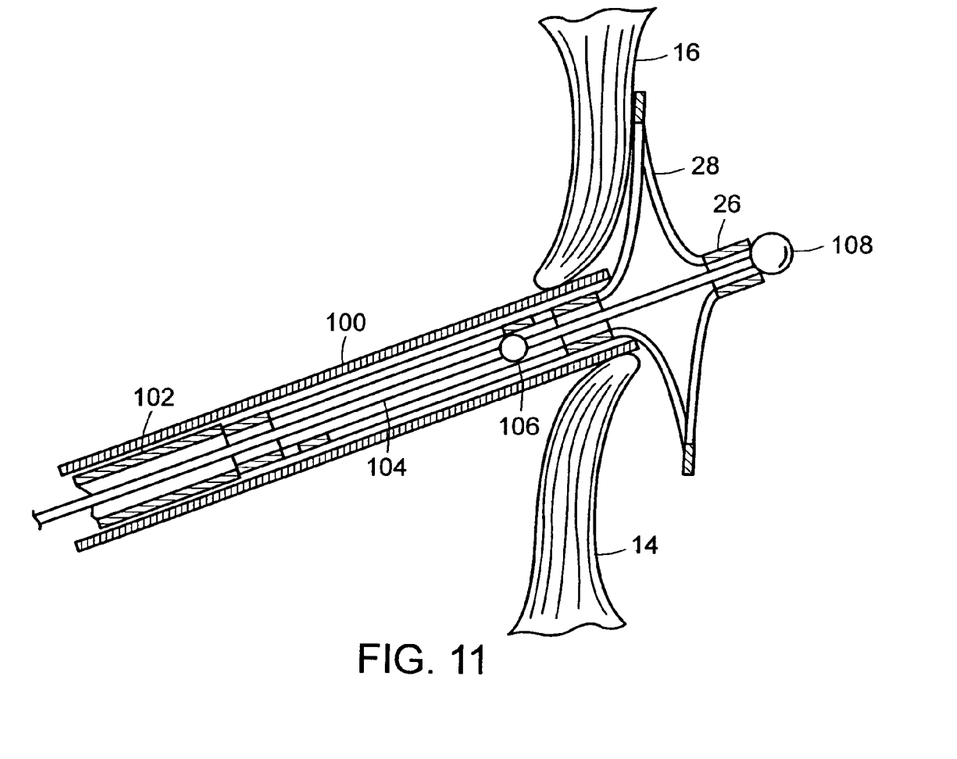

Delivery sheath 100 is first inserted into the left atrial side. Referring to FIG. 11, delivery catheter 102 is used to push the device into the left atrial side, along with wire 104, ball 106, and ball 108. Ball 106 remains within the device, while ball 108 is larger than end piece 26 and at this stage is at the distal end of the device. As the device is released from delivery sheath 100, either by pushing the device out, retracting the sheath to expose the device, or some combination of these two motions, distal side 22 can extend out radially and into contact with septum secundum 16 and septum primum 14. Side 22 expands outwardly because of a compression created by wire 104 and ball 108 preventing the device from moving further in the distal direction, and delivery catheter 102 which prevents further movement in the proximal direction.

Figure 12:
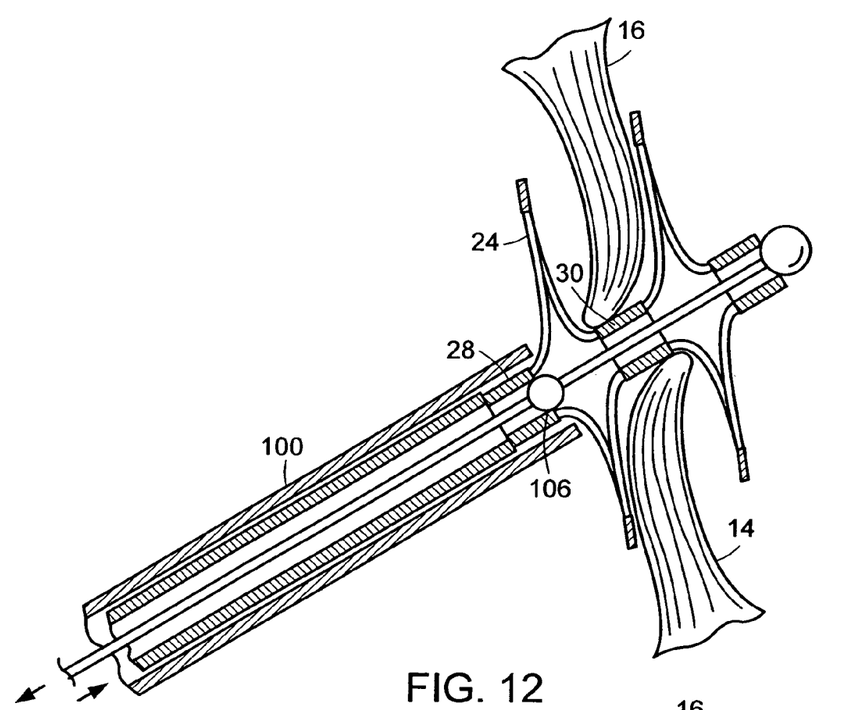

Referring to FIG. 12, the sheath 100 is further retracted to provide center joint 30 within the PFO tunnel, and then to allow the right atrial side 24 to fan out into contact with septum primum 16 and septum secundum 14. With side 24 opened in this manner and center joint 30 now much closer to end piece 28, ball 106 is up against end piece 28.

Figure 13:
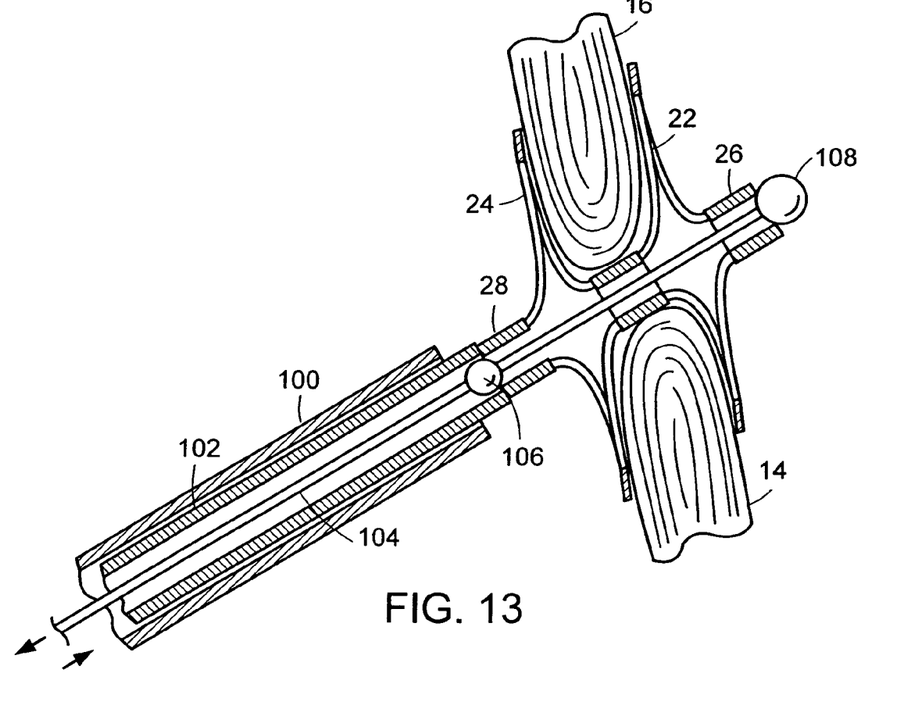

Referring to FIG. 13, wire 104 is pulled back in the proximal direction while delivery catheter 102 provides force in the distal direction sufficient to pull ball 106 through the slightly smaller opening of end piece 28, but not with enough force to pull ball 108 through end piece 26. This application of forces causes the device to fit around the PFO and form good contact with septum primum 14 and septum secundum 16.

Figure 14A:
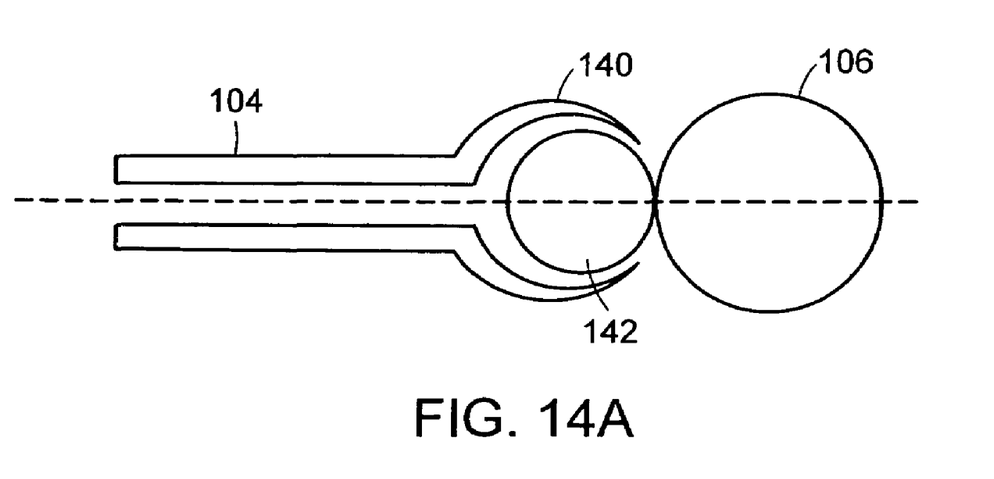
FIGS. 14A and 14B are part side, part cross-sectional views showing examples of releasable connections between a delivery wire or conduit and a catching mechanism.
Figure 14B:
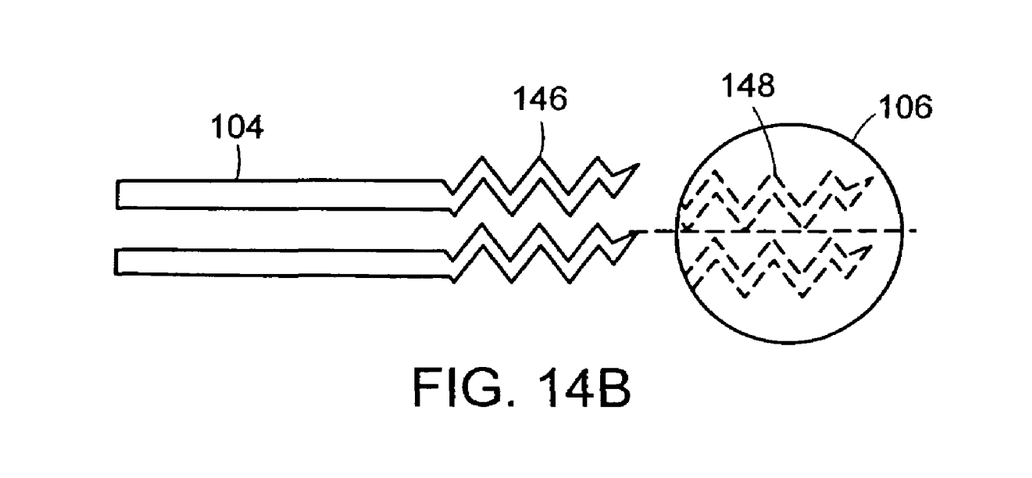

To complete the deployment, wire 104 is detached from ball 106, resulting in a positioned device similar to that shown in FIG. 6 (except that wire 104 is shown connected). Detaching wire 104 from ball 106 can be accomplished through one of a number of ways, two of which are shown in FIGS. 14A and 14B. FIG. 14A shows hollow wire 104 with grappling hooks 140. Ball 106 is rigidly connected to another smaller ball 142, sized to accommodate hooks 140. On positioning to a desired location, hooks 140 are opened and balls 142 and 106 are released together. FIG. 14B shows a hollow wire 104 with threads 146 at a distal end. These threads mate with threads 148 within ball 106. By using a wire 104 with good torqueability, wire 104 can be unscrewed from ball 106 by turning a handle (not shown) outside the body. The use of hooks or threads or other releasable techniques are generally known in the field of the delivery of medical devices.

Figure 15:
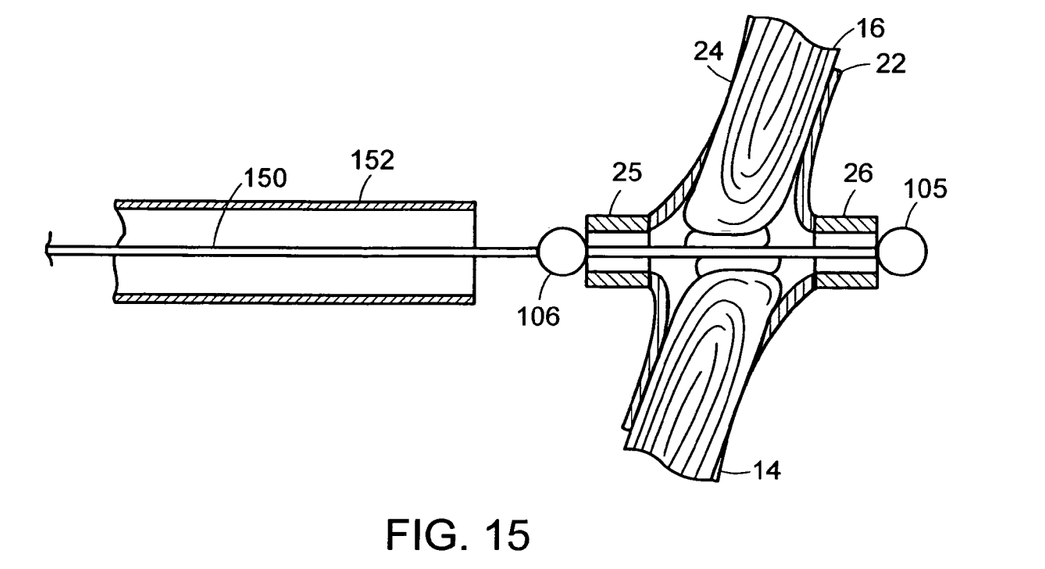
FIGS. 15-19 are part side, part cross-sectional views showing an embodiment of the recovery process for the devices deployed as described above.

FIGS. 15-19 show an embodiment for removing the device, e.g., if the operator does not like the way the device is positioned or if there are complications. FIG. 15 shows the device in the defect with only a wire 150 still attached to the proximal ball 106. The wire is within a delivery sheath 152.

Figure 16:
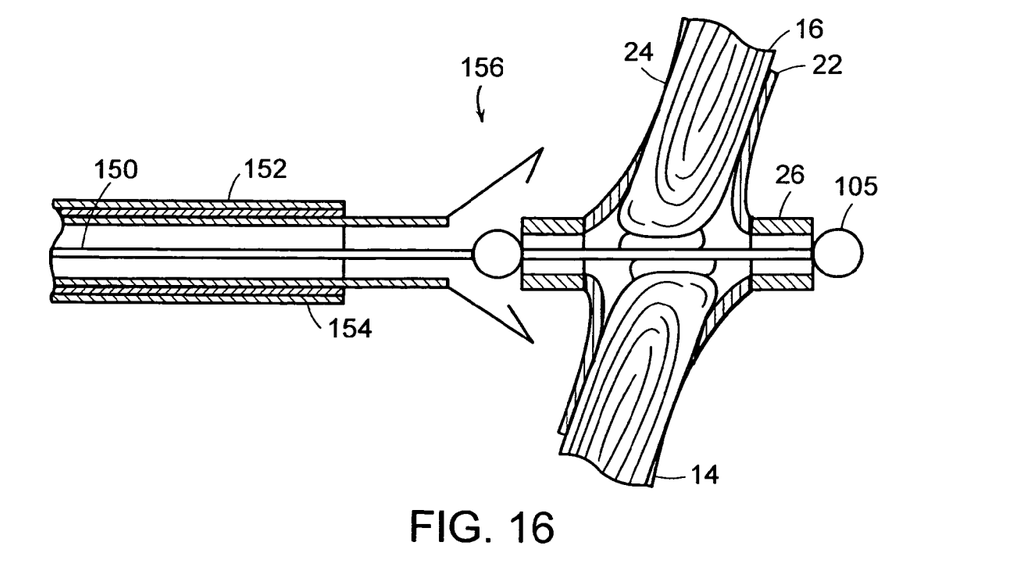
Figure 17:
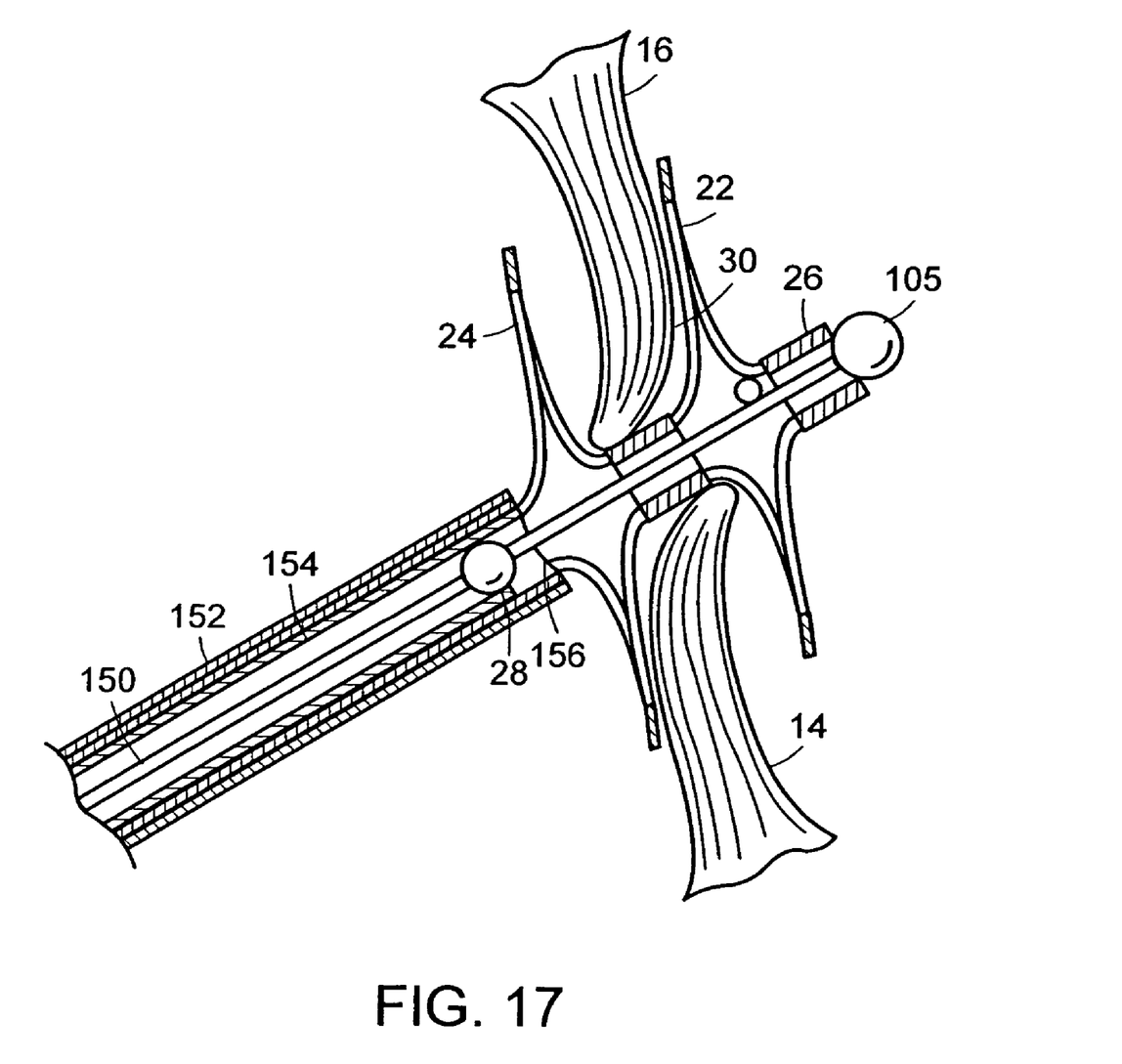
Figure 18:
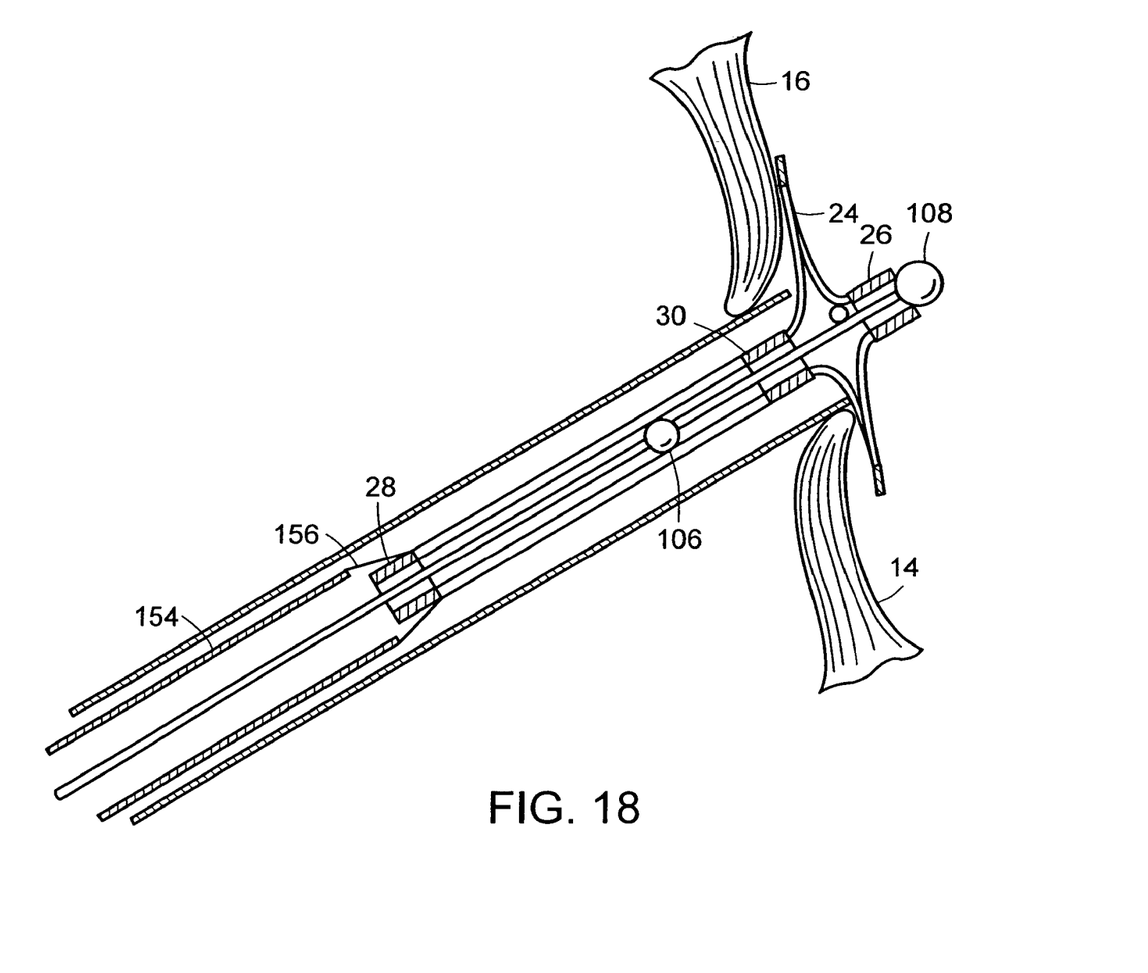

Referring to FIG. 16, to begin the recovery sequence, a recovery catheter 154 with barbs 156 is provided over wire 150. Advancing the recovery catheter exposes barbs 156. Barbs 156 can be opened and closed by the operator. Referring to FIG. 17, barbs 156 are controlled to catch on to the proximal end of the device, such as by grabbing end piece 28. Recovery catheter 154 is withdrawn, thereby pulling back end piece 28 over ball 106 and pulling the right atrial side of the device into the sheath. An opposed force can be provided on ball 106 by wire 150, which thus serves as a pusher.

Figure 19:
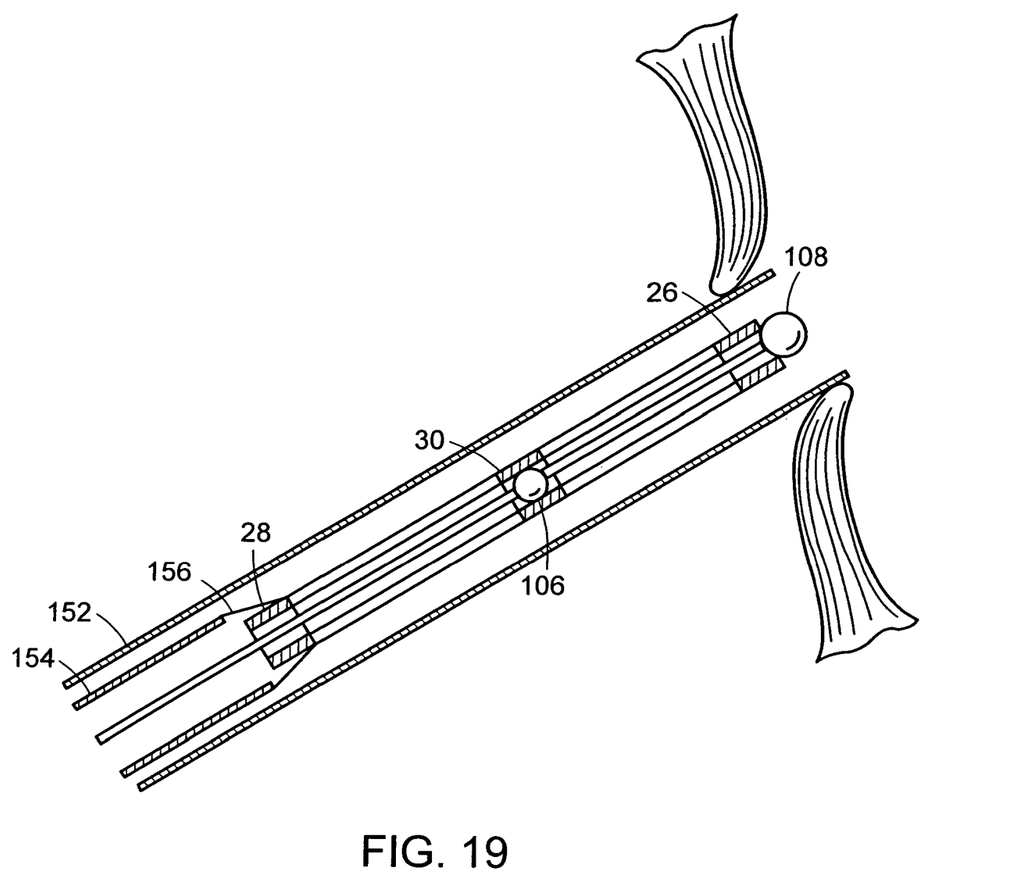

FIG. 19 shows the device fully within sheath 152 after further pulling on recovery catheter 154 causes ball 106 to pass through center joint 30, thereby allowing the left atrial side of the device to be pulled into sheath 152. Note that this process allows results in the device as shown in FIG. 19 being quite similar to that shown in FIG. 10, which is a position before delivery. Thus the device could be redeployed from this position or removed from the body.

Figure 20:
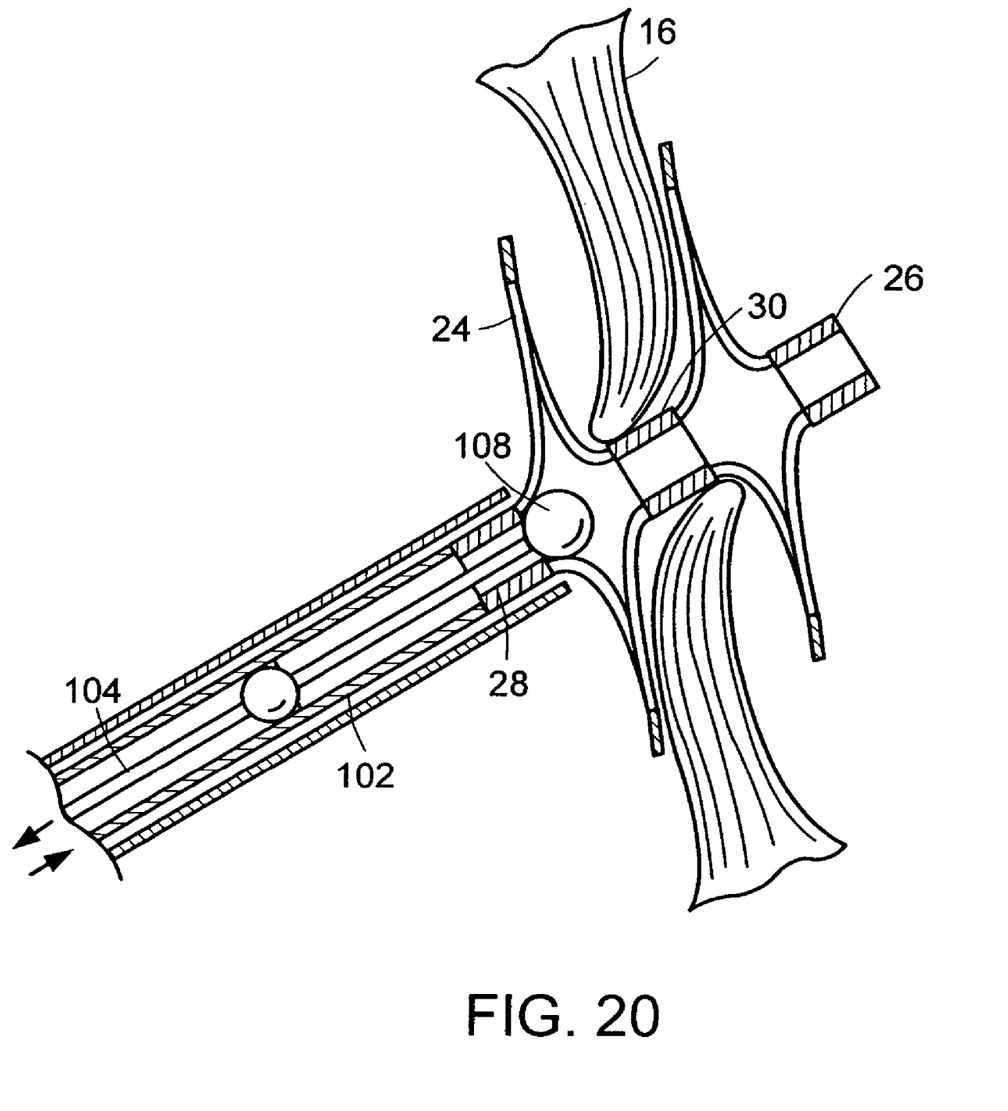
FIGS. 20-22 are part side, part cross-sectional views showing another embodiment of the recovery process for the devices deployed as described above.
Figure 21:
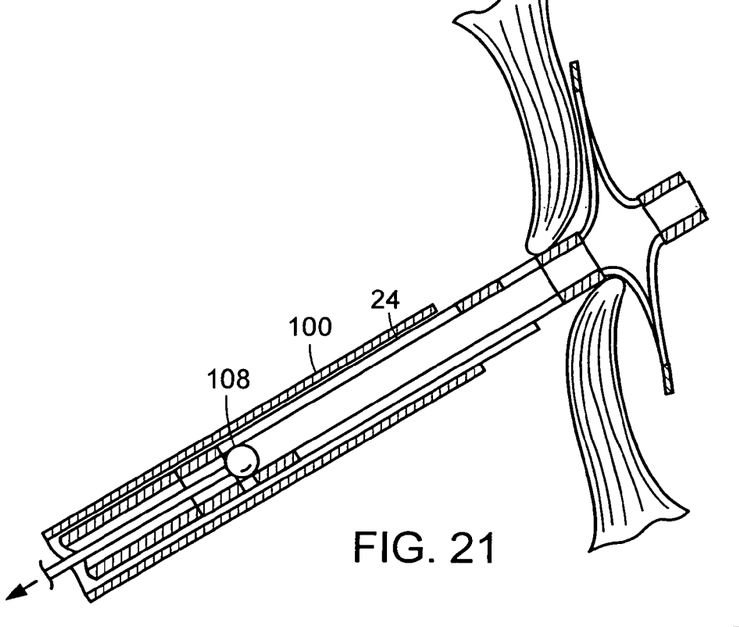
Figure 22:
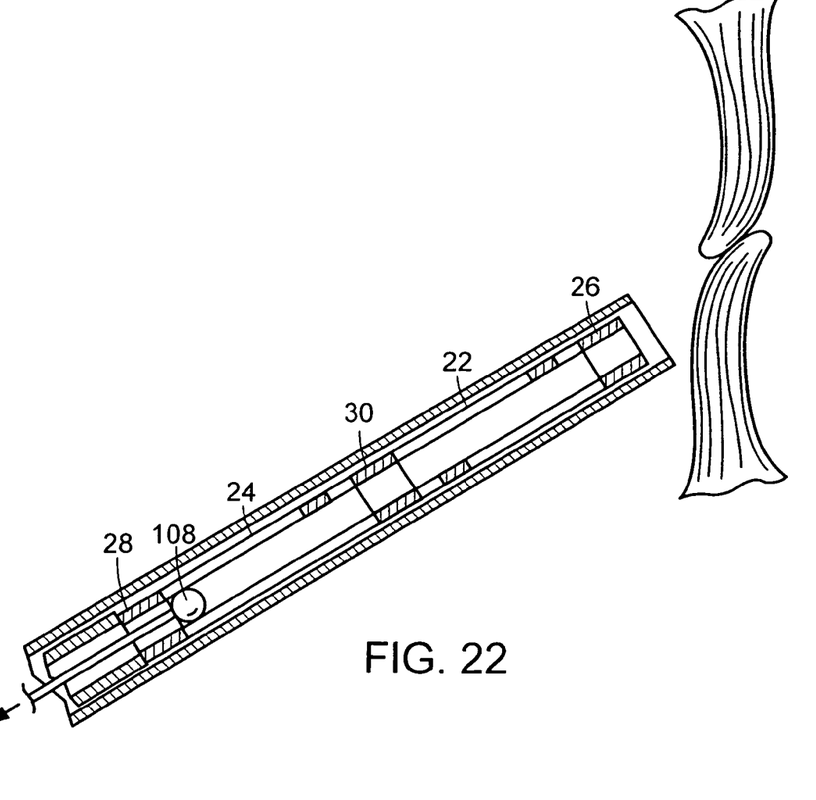

FIGS. 20-22 show another embodiment of a procedure when it is desirable to remove the device after it has been positioned, rather than leave it in the body for deployment. Referring to FIG. 20, by providing extra force on wire 104 and holding delivery catheter 102 in place, ball 108 can be pulled back through end piece 26 and center joint 30, until it rests against end piece 28.

Referring to FIG. 21, delivery catheter 102 and wire 104 are withdrawn together to pull end piece 28, to draw side 24 on the right atrial side back into delivery sheath 100. As shown in FIG. 22, further pulling of wire 104 in the proximal direction, along with delivery catheter 102, will draw the device back into the sheath, thereby allowing the device to be removed from the body.

This embodiment of FIGS. 20-22 shows a device with two balls for providing compressive forces to the device to urge it to take the final shape. It has at least one piece, in this case the delivery catheter, for holding the device to prevent proximal direction movement at the proximal side, and a piece, in this case ball 108, that can be retracted toward the proximal side provide the compressive force between the ends of the device.

Various types of catches can be used. These catches can include one or more pieces designed to latch, clamp, or otherwise lock the device in a position to help it stay in its deployed configuration. In some cases, a catch can be a latch formed integrally or monolithically with the rest of the device, and in other instances can be formed from separate pieces that are left within the body and with the device after the delivery sheaths and catheters are removed. The catch can have pieces at either end of the device to help hold it in place, or it can have pieces to hold the left atrial side and/or right atrial side separately from or in addition to holding the overall device. For example, the incorporated application being filed on an even date herewith shows examples of a right atrial side catch and a left atrial side catch with the pieces formed integrally with the device. It includes an example of a single catch that holds together both left and right atrial sides with one set of catching pieces, in this case, showing how the catching pieces can effectively be separate from the device and not be integral with the device; and an example of a device that can have one overall catch or a first catch for the left atrial side and an overall catch for the full length of the device, and also not be integral with the device.

The devices described here can be made of a metal or of a nonmetal, but are preferably made of a polymer that can be a bioresorbable polymer. If a polymer is used, it is preferably treated with a material to make it radiopaque so that it is visible under x-ray detection, or with other scanning equipment.

In embodiments described above, a spongy collar can be attached to the center joint for improved centering and to better seal the defect. The spongy collar can include a material with a drug coating or with drug impregnation to assist with healing or to provide anti-clotting agents. The device can be made with a smooth surface, or the surface can be textured, porous, or otherwise roughened to produce an inflammatory response and thereby promote faster tissue ingrowth and faster defect closure.

Having described embodiments of the invention, it should be apparent that modifications can be made without departing from the scope of the present invention as defined by scope of the claims.

What is claimed is:

1. A medical device for closing a septal defect comprising:
 a distal portion for use on one side of the septal defect and including a distal end;
 a proximal portion for use on another side of the defect and including a proximal end;
 a center joint connected to and separating the distal and proximal portions;
 the device being movable between an elongated delivery position and a compressed deployed position in which the proximal and distal ends are closer together than the proximal and distal ends are in the elongated delivery position;
 at least one of the portions including a plurality of petals configured to provide a force against the area around the septal defect, each petal including two segments extending generally radially away from a same piece selected from the distal end, proximal end, and the center joint, and a portion at the outer perimeter of the petal connecting the two segments, wherein at least one petal is further connected to an adjacent petal through a hinge that connects to one of the segments of one petal and to one of the segments of another petal.

2. The device of claim 1, wherein the segments of the petal meet at the center joint.

3. The device of claim 1, wherein the segments of the petal meet at a point spaced radially away from the center joint in the compressed deployed position.

4. The device of claim 1, wherein the segments of the petal connect to the center joint without fully converging at the center joint.

5. The device of claim 1, wherein the petals alternate such that every other petal has a vertex at the distal end or the proximal end, with the petals between them having a vertex at the center joint.

6. The device of claim 5, wherein the petals that extend away from the center joint are shorter than those that extend away from one of the distal end or the proximal end.

7. The device of claim 1, wherein the petals have substantially the same size and shape, and are evenly distributed around the circumference of the device.

8. The device of claim 1, wherein the proximal and distal portions each have petals.

9. The device of claim 1, wherein the petals on the proximal and distal portions are different on different sides of the defect.

10. The device of claim 1, wherein the septal defect has an opening, and wherein the portions, when deployed, have a roughly planar configuration in a manner that is roughly parallel to the septal defect.

11. The device of claim 1, further comprising a catch for holding the device in the compressed position, the catch compressing the end pieces.

12. The device of claim 11, wherein the catch includes first means for holding the proximal end to a center joint, and second means for holding the distal end to the center joint.

13. The device of claim 11, wherein the catch includes means for holding the proximal end to the distal end and through the center joint.

14. The device of claim 1 further comprising a tissue scaffold extending over an area defined by at least one of the petals.

15. The device of claim 14, wherein the tissue scaffold is formed of a flexible, biocompatible material capable of promoting tissue growth.

16. The device of claim 1, wherein the device is used for closing an atrial septal defects.

17. The device of claim 1, wherein the device is used for closing a patent foramen ovale (PFO).

18. The device of claim 1, wherein the device is made of a bioresorbable polymer.

19. A generally hollow tubular device having slits formed therein to produce the device of claim 1.

20. The device of claim 19, wherein the tubular device has end portions and a center portion without slits for forming petals.

21. A system including the device of claim 1, a catching mechanism for holding the device in its compressed deployed position, and a delivery system for delivering the device percutaneously and including a delivery sheath, an inner catheter for holding the device in place to prevent it from being pulled toward the proximal end when proximal movement is not desired, and a wire extending coaxially through the sheath and releasably connected to the catching mechanism.

22. A method comprising using the delivery system of claim 21 to deliver the device and catching mechanism of claim 21.

23. The method of claim 22, wherein the method is for delivering a device to a patent foramen ovale (PFO) that includes a tunnel between septum pnmum and septum secundum, the method including inserting the delivery sheath into a left atrial side, using a delivery catheter to push the device into the left atrial side, causing the distal end and the center joint to move toward each other within the left atrium into contact with septum secundum and septum primum, causing the center joint to be deployed within the tunnel, and causing the proximal end and the center joint to move toward each other within the right atrial side into contact with septum primum and septum secundum.

24. The method of claim 23, further comprising removing the device percutaneously after it has been positioned rather than leave it in the body for deployment.

* * * * *